US00PP28598P3

(12) United States Plant Patent
Clark

(10) Patent No.: US PP28,598 P3
(45) Date of Patent: Nov. 7, 2017

(54) BLACKBERRY PLANT NAMED 'APF-190T'

(50) Latin Name: ***Rubus* subgenus *Rubus* Watson**
Varietal Denomination: APF-190T

(71) Applicant: THE BOARD OF TRUSTEES OF THE UNIVERSITY OF ARKANSAS, Little Rock, AR (US)

(72) Inventor: John Reuben Clark, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 55 days.

(21) Appl. No.: 14/757,150

(22) Filed: Nov. 25, 2015

(65) Prior Publication Data

US 2017/0150665 P1 May 25, 2017

(51) Int. Cl.
*A01H 5/08* (2006.01)

(52) U.S. Cl.
USPC ..... Plt./203

(58) Field of Classification Search
USPC ..... Plt./203
CPC ..... A01H 5/0887; A01H 5/08; A01H 5/00
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark et al. |
| PP11,865 | P2 | 5/2001 | Clark et al. |
| PP14,935 | P2 | 6/2004 | Clark |
| PP15,788 | P2 | 6/2005 | Clark |
| PP16,989 | P3 | 8/2006 | Clark et al. |
| PP17,162 | P3 | 10/2006 | Clark et al. |
| PP17,983 | P2 | 9/2007 | Cabrera Avalos |
| PP20,891 | P3 | 3/2010 | Clark |
| PP22,449 | P3 | 1/2012 | Clark |
| PP23,497 | P3 | 3/2013 | Clark et al. |
| PP24,249 | P3 | 2/2014 | Clark |
| PP25,864 | P3 | 9/2015 | Clark |
| PP26,120 | P3 | 11/2015 | Clark |
| PP26,368 | P3 | 2/2016 | Banados Ortiz et al. |
| PP26,405 | P3 | 2/2016 | Clark et al. |
| PP26,413 | P3 | 2/2016 | Ortiz et al. |
| 2014/0090122 | P1 | 3/2014 | Clark |
| 2015/0020246 | P1 | 1/2015 | Clark |
| 2015/0150169 | P1 | 5/2015 | Clark et al. |
| 2015/0237785 | P1 | 8/2015 | Clark et al. |
| 2015/0351297 | P1 | 12/2015 | Clark |
| 2016/0212901 | P1 | 7/2016 | Clark et al. |

OTHER PUBLICATIONS

Lassen Canyon Nursery Blackberries Varieties 2015 retrieved on Mar. 14, 2017, retrieved from the Internet at <http://lassencanyon-nursery.com/blackberry-varieties/> 4 pp.*

University of Arkansas System Division of Agriculture Research & Extension 2015 Prime-ARK Traveler Thornless, Primocane-Fruiting Blackberry, retrieved on Mar. 14, 2017, retrieved from the Internet at <https://www.uaex.edu/farm-ranch/crops-commercial-horticulture/docs/2015_0204-Prime-Ark-Traveler-Blackberry-Popular-Description-Clark.pdf> 4 pp.*

Clark, J.R., "Division develops first thornless primocane blackberry," University of Arkansas System Division of Agriculture—Research and Extension website, Jul. 1, 2013, http://arkansasagnews.uark.edu/7751.htm 1 page.

Clark, J.R. et al., "'APF-45' Primocane-fruiting blackberry," (2011) Hort. Science 46(4):670-673.

Clark, J.R., "Osage thornless blackberry," (2013) HortScience 48:909-912.

Lowe, J.D. et al., "Primocane yield of Prime Ark 45 and Prime-Jan blackberries growing using USDA National Organic Program practices in Kentucky," (2014) J. Amer. Pomological Society 68:221-226. (Abstract) 2 pp.

Ruple, A. et al., "An evaluation of fertility in Arkansas primocane-fruiting blackberries," (2010) Hort. Science 45:1-6.

Website for Heaven Can Wait Blackberry, http://www.gurneys.com/product/heaven_can_wait_blackberry, downloaded Oct. 15, 2014 2 pp.

* cited by examiner

*Primary Examiner* — June Hwu
(74) *Attorney, Agent, or Firm* — Andrus Intellectual Property Law, LLP

(57) ABSTRACT

Description and specifications of a new and distinct blackberry cultivar named 'APF-190T' which originated from seed produced by a hand-pollinated cross of Arkansas selections A-2293T (non-patented, unreleased genotype)×APF-49T (non-patented, unreleased genotype) is provided. This new blackberry cultivar can be distinguished by its early ripening, medium to large fruit with consistent shape and size with good quality, thornless canes with excellent plant health, and primocane-fruiting habit.

5 Drawing Sheets

BLACKBERRY PLANT NAMED 'APF-190T'

Latin name: *Rubus* subgenus *Rubus* Watson.

BACKGROUND

The new primocane-fruiting cultivar of blackberry called 'APF-190T' is described herein. The new cultivar originated from a hand-pollinated cross of Arkansas selections A-2293T (unpatented selection)×APF-49T (unpatented selection) made in 2004. The seeds resulting from this controlled hybridization were germinated in a greenhouse in the spring of 2005 and planted in a field near Clarksville, Ark. (West-Central Arkansas). The seedlings fruited in the summer of 2008 and one seedling, designated 'APF-190T', was selected. It was selected for its early ripening, medium to large fruit with consistent shape and size with good quality, thornless canes with excellent plant health, and primocane-fruiting habit.

SUMMARY OF THE INVENTION

The new and distinct cultivar of blackberry originated from a hand-pollinated cross of Arkansas selections A-2293T (non-patented, unreleased genotype; female)× APF-49T (non-patented, unreleased genotype; male) made in 2004 and located near Clarksville, Ark. (West-Central Arkansas). The botanical designation of the new cultivar of blackberry is *Rubus* subgenus *Rubus* Watson.

The seeds resulting from this controlled hybridization were germinated in a greenhouse in the winter to early spring of 2005 and planted in a field near Clarksville, Ark. The seedlings fruited in the summer of 2008 on floricanes and one seedling, designated 'APF-190T', was selected for its early ripening, medium to large fruit with consistent shape and size with good quality, thornless canes with excellent plant health, and primocane-fruiting habit.

During 2008, the original plant selection was propagated asexually from root cuttings at the above-noted location, and a test row of 30 plants was established. Subsequently, a larger test planting was established with asexually multiplied plants at two locations in Arkansas. Additionally, the cultivar has been tested at a test plot in Watsonville, Calif., established from plants propagated from the test plot plants near Clarksville, Ark.

The new cultivar has been asexually multiplied annually since 2008 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

Its primocane fruiting performance is substantially better in more moderate summer climates such as Watsonville, Calif., as evidenced by larger fruit weight and higher yields compared to Clarksville, Ark. The cultivar differs from most blackberry cultivars which are floricane fruiting.

BRIEF DESCRIPTION OF THE PHOTOGRAPHS

The accompanying photographs show typical specimens of the new variety in color as nearly true as it is reasonably possible to make in a color illustration of this character. The plants shown in the figures are all three years of age.

DETAILED DESCRIPTION OF THE NEW CULTIVAR 'APF-190T'

Figure 1:
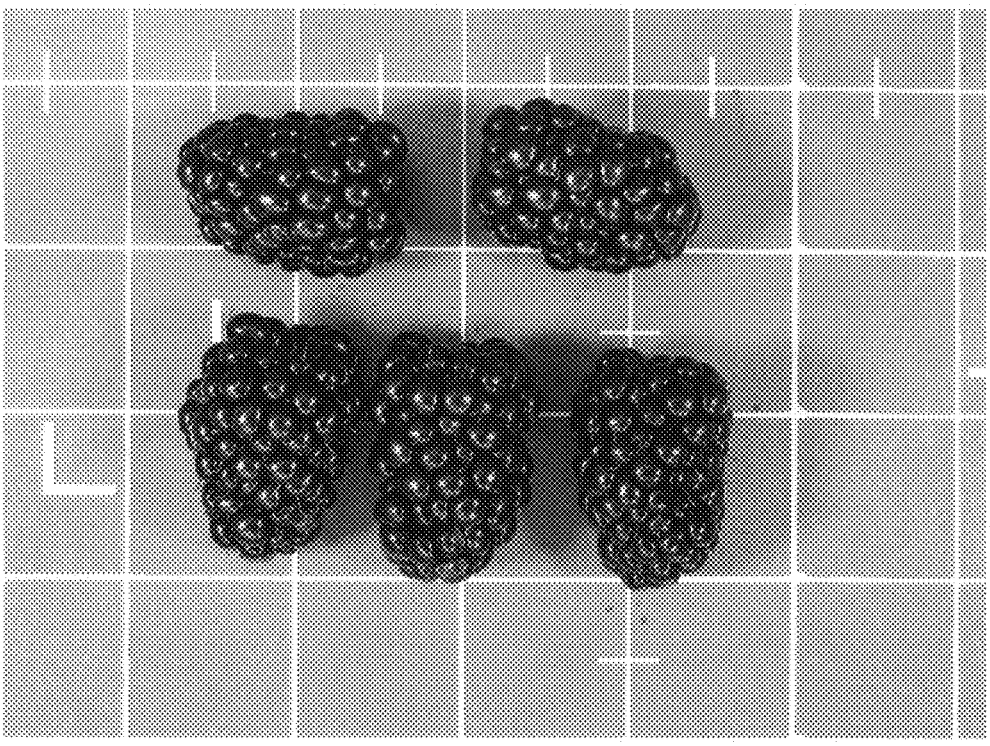
FIG. 1 is a photograph of five individual floricane fruit taken in June, near Clarksville, Ark. of 'APF-190T'.
Figure 2:
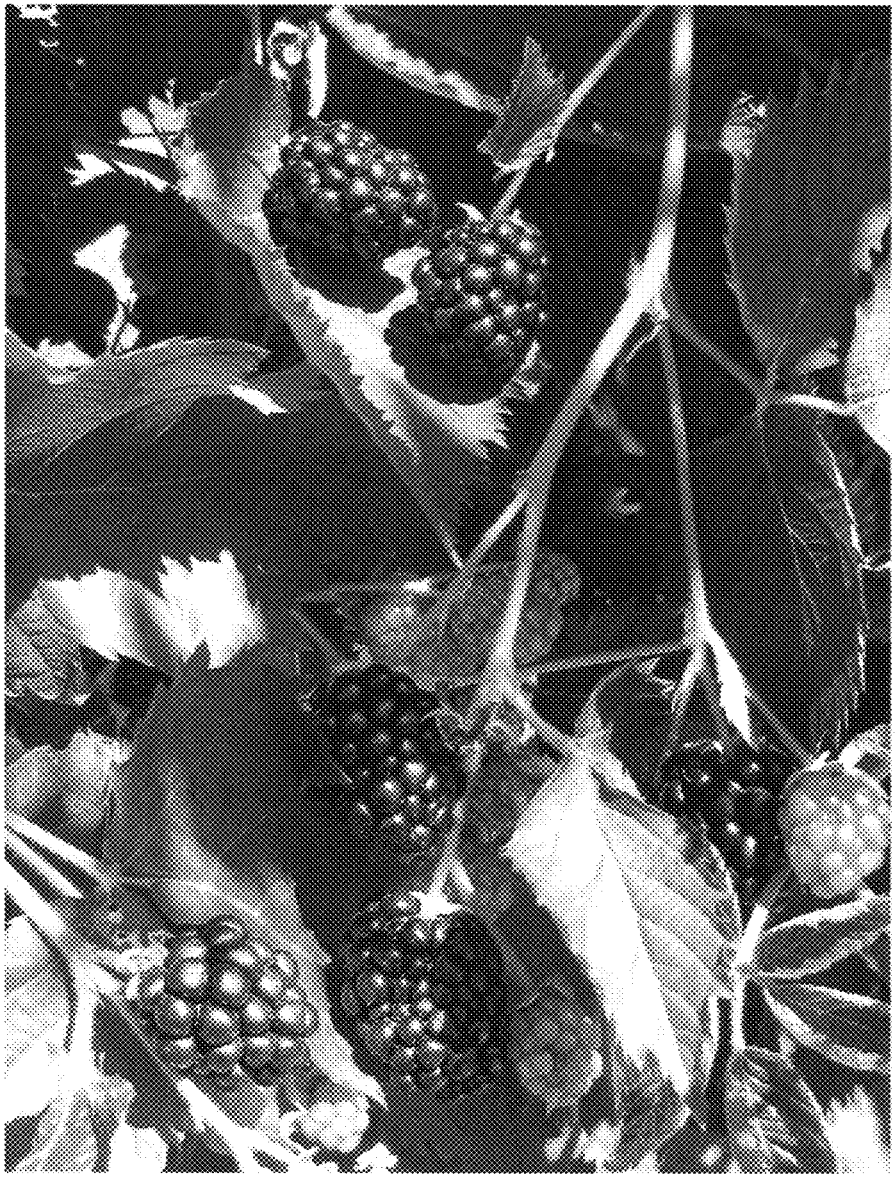
FIG. 2 is a photograph of fruits borne on a floricane taken in June near Clarksville, Ark. of 'APF-190T'.
Figure 3:
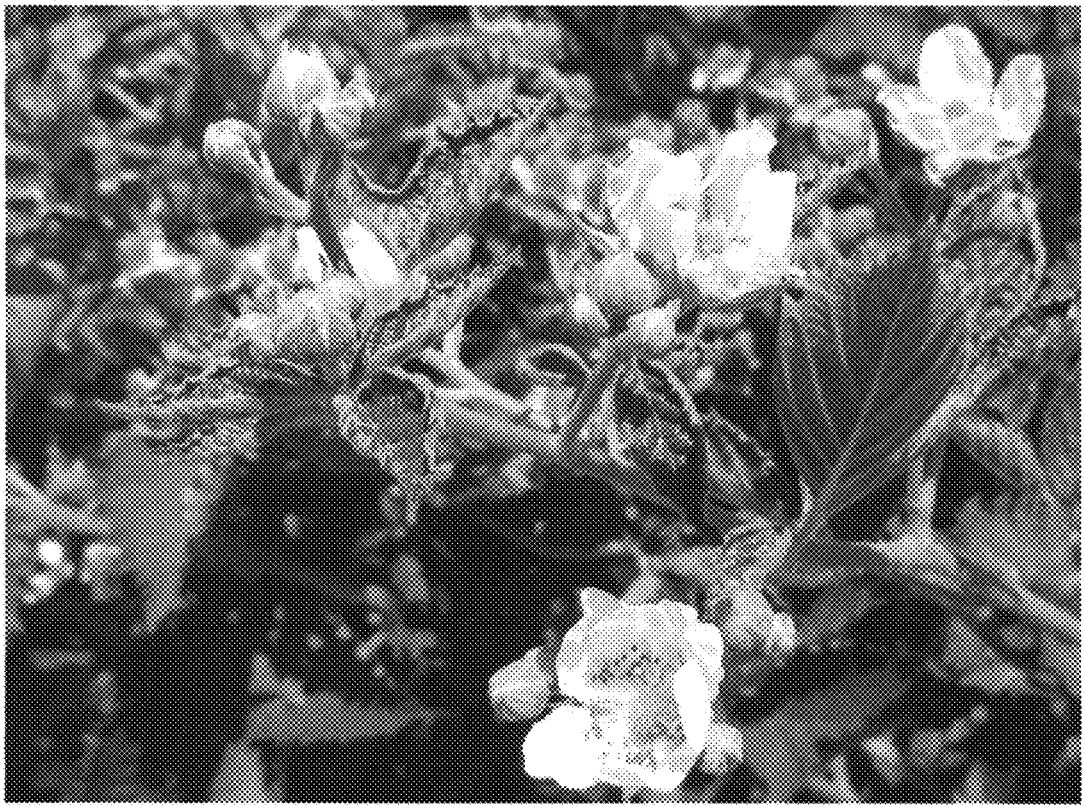
FIG. 3 is a photograph of primocane flowers and flower buds taken in July near Clarksville, Ark. of 'APF-190T'.
Figure 4:
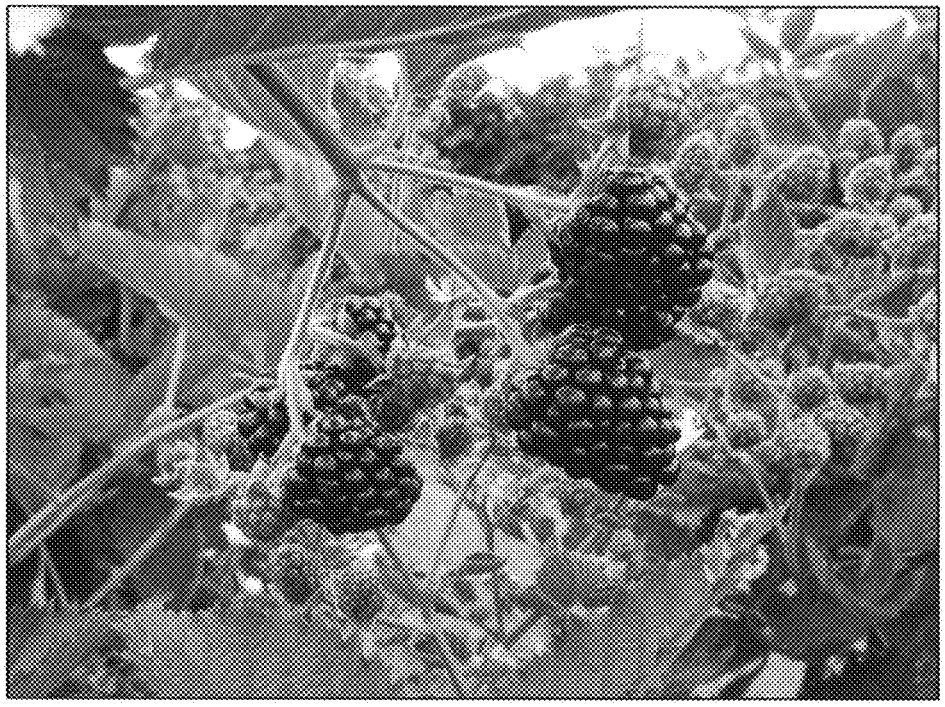
FIG. 4 is a photograph of fruit produced on a primocane taken in August near Clarksville, Ark. of 'APF-190T'.
Figure 5:
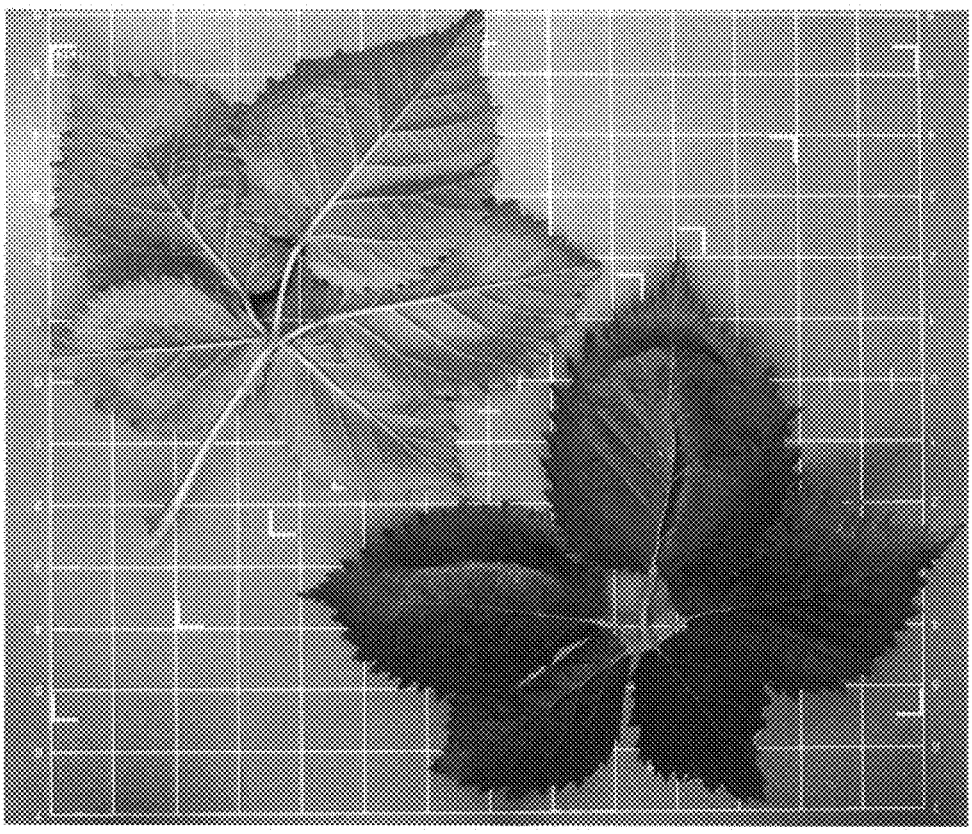
FIG. 5 is a photograph taken in June showing the abaxial (lower) and adaxial (upper) sides of primocane leaves of 'APF-190T'.

Plants and fruit of this new cultivar differ phenotypically from its parents. The new cultivar fruits on primocanes, and female parent A-2293T is floricane fruiting. The new cultivar is more productive and has larger fruit than male parent APF-49T. Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes are best managed if trained to a hedgerow and a trellis with supporting wires used to prevent canes from falling over due to wind or heavy fruit loads. The plants are thornless. Plants and fruit are moderately resistant to anthracnose [*Elsinoe veneta* (Burkh.) Jenkins], and plants have shown no evidence of susceptibility to orange rust [*Gymnoconia nitens* (Schwein.) F. Kern and H. W. Thurston.]. No screening has been done for resistance to double blossom/rosette [*Cercosporella rubi* (Wint.) Plakidas].

The floricane bloom period of the new cultivar begins on 2 May, compared to 24 April for 'APF-45' (U.S. Plant Pat. No. 22,449) and is comparable in length compared to 'APF-45'. Primocane bloom period begins 20 June compared to 30 June for 'APF-45'.

Floricane fruit of the new cultivar begins ripening 7 June, 6 days later than 'APF-45', and has a comparable fruiting period of about 39 days compared to 'APF 45' of 40 days. Primocane first ripe fruit date was 30 of July on tipped primocanes and ripened earlier than 'APF-45' of 8 August. Primocane fruit harvest can continue until harvest with appropriate environmental conditions, the most important being temperatures below 32° C. (90° F.).

Fruit yields of the new cultivar on floricanes are usually 1.4 kg/plant (3.1 lb) if the floricanes are retained for fruiting, compared to 1.8 kg/plant (4.0 lb) for 'APF-45' in West-Central Arkansas. Fruit yields of the cultivar on primocanes in West-Central Arkansas average 0.6 kg (1.3 lb/plant) compared to 0.8 kg (1.8 lb/plant) for 'APF-45'. Primocane yields in Watsonville, Calif. average 4-5.5 kg/plant (8.8 to 12.1 lb).

The fruit is conical elongated to blocky in shape, bright glossy black in color, and very attractive. The floricane fruit is large (6.7-7.5 g). Primocane fruit in West-Central Arkansas of the new cultivar averaged 4.7-7.2 g/berry while 'APF-45' averaged 5.7-7.3 g/berry, and in Watsonville, Calif. averaged 7.0 g/berry. Storage (shipping) potential of fresh fruit of the new cultivar is comparable to that of 'APF-45'.

The fresh fruit rates very good in flavor, comparable to 'APF-45', higher than for 'Natchez' (U.S. Plant Pat. No. 20,891), but not as high as for 'Ouachita' (U.S. Plant Pat.

No. 17,162). The flavor is sweet and sub-acid, with a distinct blackberry aroma. The soluble solids concentration averages 9.7 to 10.5% on shiny black fruit harvested from floricanes but can extend to 13.2% for primocane fruit. Floricane fruit and flower clusters are medium-large, cymose, and are mostly borne on the periphery of the plant canopy, providing easy access to harvest. Flower fertility is high and clusters are well filled.

Primocane fruit and flowers are borne on the cane terminus or on lateral branches if primocanes are tipped, and fruiting continues down the primocane during the season. Canes usually attain a length of 1.5 to 1.8 m (4-5 ft) prior to the appearance of flower buds. The number of nodes down the cane that develop flowers is largely dependent on the length and conditions of the late summer to fall growing period.

The following is a detailed description of the botanical and pomological characteristics of the subject blackberry. Color data are presented in Royal Horticultural Society Colour Chart designations (1986 2nd edition). Where dimensions, sizes, colors, and other characteristics are given, it is to be understood that such characteristics are approximations of averages set forth as accurately as practicable.

Plants used for botanical data were three years old and grown on a fine sandy loam soil with trickle irrigation near Clarksville, Ark. The plants were fertilized near budbreak (late March on average) with complete or nitrogen fertilizer, and had an additional nitrogen fertilizer application in early July. Primocanes were tipped at approximately 1.35 m (53 inches), and grown in a hedgerow training system. Weeds were controlled with pre- and postemergence herbicides supplemented with mechanical weed control activities. A single application of liquid lime sulfur was applied to the plants at budbreak, but no other fungicides were used. The descriptions reported herein are from specimens grown near Clarksville, Ark. unless otherwise noted.

Plant:

*Size*.—Medium. Plants are grown in a hedgerow and primocanes tipped at approx. 135 cm; plants in this system range in size from approx. 135-140 cm tall and 91-102 cm wide.

*Growth habit*.—Moderate vigor, canes erect; suckers primarily from the crown.

*Growth rate*.—First emergence of primocanes is 5 April and primocanes reach tipping height (135 cm) approximately 24 May.

*Productivity*.—Floricane — 1.1 kg/plant (2.4 lb) compared to 1.3 kg/plant (2.9 lb) for 'APF-45'. Primocane — 0.6 kg/plant (1.3 lb), compared to 0.8 kg/plant (1.8 lb) for 'APF-45' but in Watsonville, Calif. achieves 5.5 kg/plant (12.1 lb).

*Cold hardiness*.—Hardy to −13-−15° C. (4-8° F.) or lower, comparable to 'APF-45'.

*Canes*.—Thornless, erect. Floricane (dormant or winter cane): Cane diameter: base 1.60 cm; midpoint 1.34 cm; terminal 0.99 cm. Internode length: base 8.96 cm; midpoint 6.31 cm; terminal 5.07 cm. Floricane color: base Yellow-green group 146-B; midpoint Yellow-green group 146-B; terminus Yellow-green group 146-C. Primocane (current-season cane): Cane diameter: base 1.67 cm; midpoint 1.29 cm; terminal 0.70 cm. Internode length: base 5.09 cm; midpoint 6.44 cm; terminal 3.15 cm. Primocane color: base Yellow-green group 144-A; midpoint Yellow-green group 144-A; terminus Yellow-green group 144-A. Anthocyanin coloration seen only on young shoot tips of lateral branches. Date of primocane emergence: 5 April. Lateral branching after tipping (measured at the end of growing season): Average number of lateral branches: 9.8; distribution primarily in the top half of the cane.

*Disease resistance*.—Moderate resistance to anthracnose, and plants appear. Not susceptible to orange rust. No screening has been done for resistance to double blossom/rosette.

Foliage:

*Leaf bud burst*.—Medium bud burst for 'APF-190' averaged February 24 and this bud burst is considered medium.

*Floricane*.—Leaves: Medium; mature compound leaf width 14.25 cm; length 10.08 cm. Glossiness abaxial: dull, no pubescence; adaxial: dull, no pubescence. Shape: palmate. Leaflet: Width 6.53 cm; Length 8.68 cm; Shape: ovate with acute apex and subcordate base; margin serrated; serration teeth length: 0.58 cm and width at base: 0.60 cm; pubescence: very light (older) to medium (younger) depending on age; pubescence on abaxial surface only on veins and none on the adaxial surface; number of leaflets per compound leaf: 3. Color: Base abaxial: Green Group (137A); adaxial: Green Group (137D); Midpoint abaxial: Green Group (137A); adaxial: Green Group (137D); Terminal abaxial: Green Group (137A); adaxial: Green Group (137D). Petioles: Length: 6.29 cm; Color: Yellow-Green Group (145A); texture: slightly bumpy; moderate pubescence. Petiolules: Length: 1.52 cm; Color: Grayed-orange (176B); texture: slightly bumpy on adaxial side; moderate pubescence. Stipules: Length 1.63 cm; width: 0.36 cm. Shape: Overall: deltoid; apex: acute; margin: entire (smooth); base: truncate. Texture: Abaxial: heavy pubescence; adaxial: heavy pubescence. Color: Abaxial: Green-group 137D; adaxial: Green-group 138D.

*Primocane*.—Leaves: Large; mature compound leaf width 25.86 cm; length 22.44 cm. Shape: Palmate. Glossiness: Abaxial: low to no gloss; adaxial: moderately glossy when young, loses gloss as it matures. Leaflet: Width 10.22 cm; length: 12.87 cm; shape: ovate with acute apex and cordate base; margin: serrated; serration teeth length: 0.63 cm; width at base: 0.58 cm; pubescence: present on abaxial surface only on veins, light to none on adaxial surface; number of leaflets per compound leaf: 5. Color: base abaxial Green Group (137C); adaxial Green Group (137A); midpoint abaxial Green Group (137C); adaxial Green Group (137A); terminal abaxial Green Group (137C); adaxial Green Group (137A). Petioles: Length 6.78 cm; color: mix of Yellow-green Group (145A) and Greyed-orange group 176B; texture: light pubescence. Petiolules: Length 3.47 cm; color abaxial: Yellow-green Group (145A); adaxial: Greyed-orange Group 176B; texture: light pubescence. Stipules: Length 0.82 cm; width: 0.62 cm. Shape: Overall: lanceolate; apex: acuminate; margin: entire (smooth). Base: truncate. Texture: Abaxial: heavy pubescence; adaxial: heavy pubescence. Color: Abaxial: Green-group 137D; adaxial: Green-group 138D.

Flowers:

*Floricane*.—Date of bloom: 10% bloom 2 May, compared to 24 April for 'APF-45'; 50% bloom 6 May compared to 'APF-45' 2 May. Petal color: Abaxial: White Group (155D); adaxial: White Group 155-D.

*Reproductive organs*.—Stamens — erect, numerous. Pistils — numerous. Pollen — normal, fertile, and abundant. Flower diameter: 3.99 cm. Flower depth: 1.26 cm. Petal size: Length 2.05 cm; width 1.70 cm. Petal Shape: Apex: rounded; margin: entire (smooth); base: acuminate. Petal Texture: Abaxial: no pubescence; adaxial; no pubescence. Average number flowers per cluster: 3.4. Average number of petals per flower: 5. Sepals: Length 1.39 cm; width: 0.53 cm. Sepals shape: Overall: deltoid; apex: acute; margin: entire (smooth); base: truncate. Sepals texture: Abaxial: heavy pubescence; adaxial: heavy pubescence. Sepals color: Abaxial: Green-group 138D; adaxial: Green-group 137D. Number of sepals per flower: 5. Pedicle length: 4.27 cm; Color: Yellow-green Group 145A; texture: heavy pubescence. Peduncle size: length: 2.05 cm; width: 1.70 cm. Peduncle color: Green Group (143C). Cyme type: Elongated compound cyme; Length: 11.62 cm.

*Primocanes*.—Date of bloom: First bloom 20 June compared to 30 of June for 'APF-45', and can extend until frost depending on environment and cultural management. Petal color: Abaxial: White Group (155D); adaxial: White Group 155-D. Reproductive organs: Stamens — numerous. Pistils — numerous. Pollen — fertile and abundant unless temperatures exceed 32° C. (90° F.) at which temperature can damage flowers including anthers and pollen production can be reduced. Flower diameter: 2.88 cm. Petal size: Length: 1.69 cm; width: 1.14 cm. Petal Shape: Apex: rounded; margin: entire (smooth); base: curveate. Petal Texture: Abaxial: no pubescence; adaxial; no pubescence. Average number flowers per cluster: 19.2. Average number of petals per flower: 5.4. Sepals: Length: 0.82 cm; width: 0.62 cm. Sepals shape: Overall: lanceolate; apex: acuminate; margin: entire (smooth); base: truncate. Sepals texture: Abaxial: heavy pubescence; adaxial: heavy pubescence. Sepals color: Abaxial: Green-group 137D; adaxial: Green-group 138D. Number of sepals per flower: 5. Pedicle length: 3.48 cm; Color: Green Group 137D; texture: heavy pubescence. Peduncle size: length: 4.99 cm; width: 1.68 cm. Peduncle color: Green Group 137C. Cyme type: Elongated cyme; Length: 14.86 cm.

Fruit:

*Floricane*.—Maturity — Average first ripe date 7 June, 6 days later than 'APF-45', and has a comparable fruiting period of about 39 days compared to 'APF 45' of 40 days. Size: Large, average 6.7-7.5 g. Diameter of fruit at primary position on inflorescence: equator 2.19 cm; base pole 1.43 cm; terminal pole 1.89 cm. Diameter of fruit at secondary positions on inflorescence: equator 2.10 cm; base pole 1.72 cm; terminal pole 1.17 cm. Length (primary fruit): 3.37 cm. Length (secondary fruit): 2.82 cm. Length (tertiary fruit): 2.28 cm. Shape: conical elongated to blocky. Color: Black Group (202A). Drupelet size: 0.52 cm. Drupelets per berry: 96. Seed size: Length: 3.89 mm; width: 2.45 mm. Seed weight: Wet: 8.5 mg; dry: 3.28 mg. Seed color: Wet: Grayed-orange 165B; dry: Grayed-yellow 161B. Soluble solids: 9.7-10.5% on shiny black fruit. pH: 3.2-3.4. Acidity: 0.8 to 0.9% citric acid. Processed quality: Not evaluated for processing. Uses: Local or commercial shipping markets as it has good handling potential and postharvest storage performance for shipping. Postharvest evaluations for floricane fruits stored for 7 days at 5° C., 80% relative humidity indicated good performance for 'APF-190T'. Evaluations indicated 'APF-190T' storage potential was similar to industry standards 'Ouachita', (U.S. Plant Pat. No. 17,162) and (U.S. Plant Pat. No. 22,449) 'Prime-Ark® 45'. Percent of berries with red drupe, percent soft berries and percent berries with leak among these three cultivars were similar and resulted in longer storage than the commercial standard 'Tupy'.

*Primocane*.—Maturity — First ripe fruit date 30 of July on tipped primocanes and ripens earlier than 'APF-45' of 8 August and can fruit until frost depending on environment and cultural management. Size: Medium, 4.7 to 7.2 g/berry. Diameter of fruit at primary position on inflorescence: equator 2.20 cm; base pole 1.91 cm; terminal pole 1.20 cm. Diameter of fruit at secondary positions on inflorescence: equator 2.01 cm; base pole 1.71 cm; terminal pole 0.99 cm. Length (primary fruit): 2.47 cm. Length (secondary fruit): 2.12 cm. Length (tertiary fruit): 1.97 cm. Shape: conical elongated to blocky. Color: Black Group (202A). Drupelet size: 0.53 cm. Drupelets per berry: 68. Seed size: Length: 4.19 mm; width: 2.77 mm. Seed weight: Wet: 9.3 mg; dry: 5.4 mg. Seed color: Wet: Grayed-orange 167C; dry: Grayed-orange 164D. Soluble solids: 9.7 to 10.5%. pH: 3.3 to 3.4. Acidity: 0.5 to 0.9% citric acid. Processed quality: Not evaluated for processing. Uses — Local or commercial shipping markets as it has good handling potential and postharvest storage performance for shipping.

*The cultivar*.—The most distinctive features of the cultivar are early ripening, medium to large fruit with consistent shape and size with good quality, thornless canes with excellent plant health, and primocane-fruiting habit.

I claim:

1. A new and distinct cultivar of blackberry plant named 'APF-190T', substantially as illustrated and described.

* * * * *